United States Patent
Ben-Dor et al.

(10) Patent No.: US 10,473,580 B2
(45) Date of Patent: Nov. 12, 2019

(54) PORTABLE SOIL SPECTRAL PROBE

(71) Applicant: RAMOT AT TEL-AVIV UNIVERSITY LTD., Tel Aviv (IL)

(72) Inventors: Eyal Ben-Dor, Rishon LeZion (IL); Amihai Granot, D.N. Hof Ashkelon (IL)

(73) Assignee: Ramot at Tel-Aviv University Ltd., Tel Aviv (IL)

(*) Notice: Subject to any disclaimer, the term of this patent is extended or adjusted under 35 U.S.C. 154(b) by 251 days.

(21) Appl. No.: 15/407,295

(22) Filed: Jan. 17, 2017

(65) Prior Publication Data
US 2017/0205335 A1    Jul. 20, 2017

Related U.S. Application Data

(60) Provisional application No. 62/278,471, filed on Jan. 14, 2016.

(51) Int. Cl.
*G01J 3/46* (2006.01)
*G01N 21/25* (2006.01)
*G01J 3/02* (2006.01)
*G01N 21/31* (2006.01)
*G01N 33/24* (2006.01)

(52) U.S. Cl.
CPC .......... *G01N 21/255* (2013.01); *G01J 3/0262* (2013.01); *G01N 21/31* (2013.01); *G01N 33/24* (2013.01)

(58) Field of Classification Search
CPC ... G01N 2201/0221; G01N 2201/1211; G01N 33/24

USPC ......................................................... 356/402
See application file for complete search history.

(56) References Cited

U.S. PATENT DOCUMENTS

| | | |
|---|---|---|
| 5,038,040 A | 8/1991 | Funk et al. |
| 5,128,882 A | 7/1992 | Cooper et al. |
| 7,408,145 B2 | 8/2008 | Holland |
| | (Continued) | |

FOREIGN PATENT DOCUMENTS

| | | |
|---|---|---|
| CN | 101881725 | 11/2010 |
| CN | 102680413 | 9/2012 |
| | (Continued) | |

OTHER PUBLICATIONS

Dinesh Babu Madhavan et al; An assessment of diffuse reflectance mid-infrared spectroscopy for measuring soil carbon, nitrogen and microbial biomass; 19th World Congress of Soil Science, Soil Solutions for a Changing World Aug. 1-6, 2010, Brisbane, Australia. Published on DVD.

*Primary Examiner* — Sunghee Y Gray
(74) *Attorney, Agent, or Firm* — A.C. Entis-IP Ltd.; Allan C. Entis

(57) ABSTRACT

Apparatus for measuring spectral reflectance of a surface, the apparatus comprising: a chamber comprising a wall formed having an aperture defined by an aperture boundary; a light source mounted to the chamber and having a field of illumination (FOI) configured to intersect the aperture at an illumination intersection; and an optical fiber mounted to the chamber and having a field of view (FOV) configured to intersect the aperture at an imaging intersection; wherein the chamber is configured so that when the aperture is positioned on a surface the chamber substantially prevents light from entering a volume of the chamber.

19 Claims, 3 Drawing Sheets

(56) References Cited

U.S. PATENT DOCUMENTS

| | | | |
|---|---|---|---|
| 8,204,689 | B2 | 6/2012 | Christy et al. |
| 8,472,023 | B2 | 6/2013 | Preiner et al. |
| 2003/0136916 | A1 | 7/2003 | Kearfott et al. |
| 2006/0158652 | A1 | 7/2006 | Rooney et al. |
| 2015/0086425 | A1* | 3/2015 | Fujimura ............... G01N 21/05 422/69 |
| 2015/0204041 | A1 | 7/2015 | Chang |
| 2015/0343560 | A1* | 12/2015 | Pettit ................. B23K 26/0006 219/121.62 |

FOREIGN PATENT DOCUMENTS

| | | |
|---|---|---|
| CN | 202793590 | 3/2013 |
| CN | 203981573 | 12/2014 |
| DE | 102011117713 | 1/2013 |

\* cited by examiner

PORTABLE SOIL SPECTRAL PROBE

RELATED APPLICATIONS

The present application claims the benefit under 35 U.S.C. 119(e) of U.S. Provisional Application 62/278,471 filed on 14 Jan. 2016, the disclosure of which is incorporated herein by reference.

TECHNICAL FIELD

Embodiments of the disclosure relate to apparatus and methods for measuring in situ spectral reflectance of soil.

BACKGROUND

Information about the surface components of the ground, for example, its rocks, soils, sand, vegetation, and artificial land covers such as asphalt and concrete, is used in understanding, monitoring, and modeling properties of soils, and for determining how to protect the environment. In the field of soil science, information characterizing the composition and composition of ground soils, hereinafter also referred to simply as soil, is used to improve soil and crop quality. Properties of soil and soil quality are routinely determined through laboratory analysis of collected soil samples. Reflectance spectroscopy of soil samples provides measurements of a spectrum of light reflected by a soil sample from a known spectrum of light illuminating the soil to provide data for assessing attributes of the soil.

SUMMARY

An aspect of an embodiment of the disclosure relates to providing a portable apparatus, hereinafter also referred to as a soil field probe (SoilPro) for in situ measuring properties of light reflected from soil comprised in a region of an area of land to provide a reflectance spectrum for the soil.

In an embodiment of the disclosure, a SoilPro comprises a chamber having an aperture configured to be placed over a surface, object, or substance, such as a region of soil, hereinafter also referred to as a "land sample", in an area of land, and a light source mounted to the chamber for illuminating the land sample that is located at the aperture. The light source has a field of illumination (FOI) and is mounted to the chamber so that an intersection, which may be referred to as an "illumination intersection", of the FOI and a plane that substantially includes a boundary of the chamber aperture, lies substantially within the aperture boundary. Optionally, the illumination intersection is substantially congruent with the chamber aperture. An optical fiber is mounted to the chamber so that a first end, hereinafter also referred to as a "collecting end", of the fiber collects light from the light source that is reflected by the land sample. A field of view (FOV), hereinafter also referred to as an instantaneous field of view (IFOV), of the optical fiber determined by the fiber's numerical aperture (NA), intersects the plane of the chamber aperture. In an embodiment, the intersection of the IFOV and the aperture plane, which may be referred to as an "imaging intersection", lies substantially within the chamber aperture boundary so that it overlaps with at least a portion of the illumination intersection. Optionally, the imagining intersection is substantially congruent with the illumination intersection.

In an embodiment, the optical fiber is mounted to a collimator connected to the chamber. The collimator is, optionally funnel shaped, and is configured to collimate light so that during operation of the SoilPro, light collected by the collecting end of the optical fiber is substantially limited to light from the light source that directly illuminates the land sample and is directly reflected to the collecting end of the optical fiber by the land sample. Light collected by the collecting end of the optical fiber propagates along the fiber to a second end, which may be referred to as "output end", of the fiber from which the light may be directed to a spectrometer.

Optionally, SoilPro comprises a camera configured to image the land sample. Optionally, SoilPro comprises a laser pointer mounted to the chamber and configured to illuminate a land sample at the chamber aperture to provide a point of reference, hereinafter also referred to as a fiducial, in the land sample. In an embodiment, SoilPro comprises a communication interface operable to support wire or wireless communication between SoilPro and a controller that controls operation of SoilPro and/or apparatus for storing and/or processing data provided by SoilPro. The wireless communication interface may comprise any suitable radio interface and may, by way of example, comprise at least one and/or any combination of more than one of an interface to a mobile phone network, a Bluetooth interface, and/or a WiFi interface.

In an embodiment of the disclosure the SoilPro light source is controllable to be moved to illuminate the land sample from different positions and orientations, inside the chamber. A position and orientation from which the light source illuminates the land sample is referred to as a pose of the light source. In an embodiment SoilPro comprises a controller that controls the light source to illuminate the land sample from a plurality of different light source poses. For each pose, the controller optionally controls the camera to image the land sample and the optic fiber and spectrometer to acquire a reflectance spectrum of light reflected by the land sample from light transmitted by the light source to illuminate the land sample. The images and spectra acquired for the different poses may be analyzed to distinguish specular from Lambertian reflection of light by the land sample and/or provide an improved a signal to noise ratio (SNR) for the reflectance spectrum.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical features that appear in more than one figure are generally labeled with a same label in all the figures in which they appear. A label labeling an icon representing a given feature of an embodiment of the invention in a figure may be used to reference the given feature. Dimensions of features shown in the figures are chosen for convenience and clarity of presentation and are not necessarily shown to scale.

DETAILED DESCRIPTION

Figure 1A:
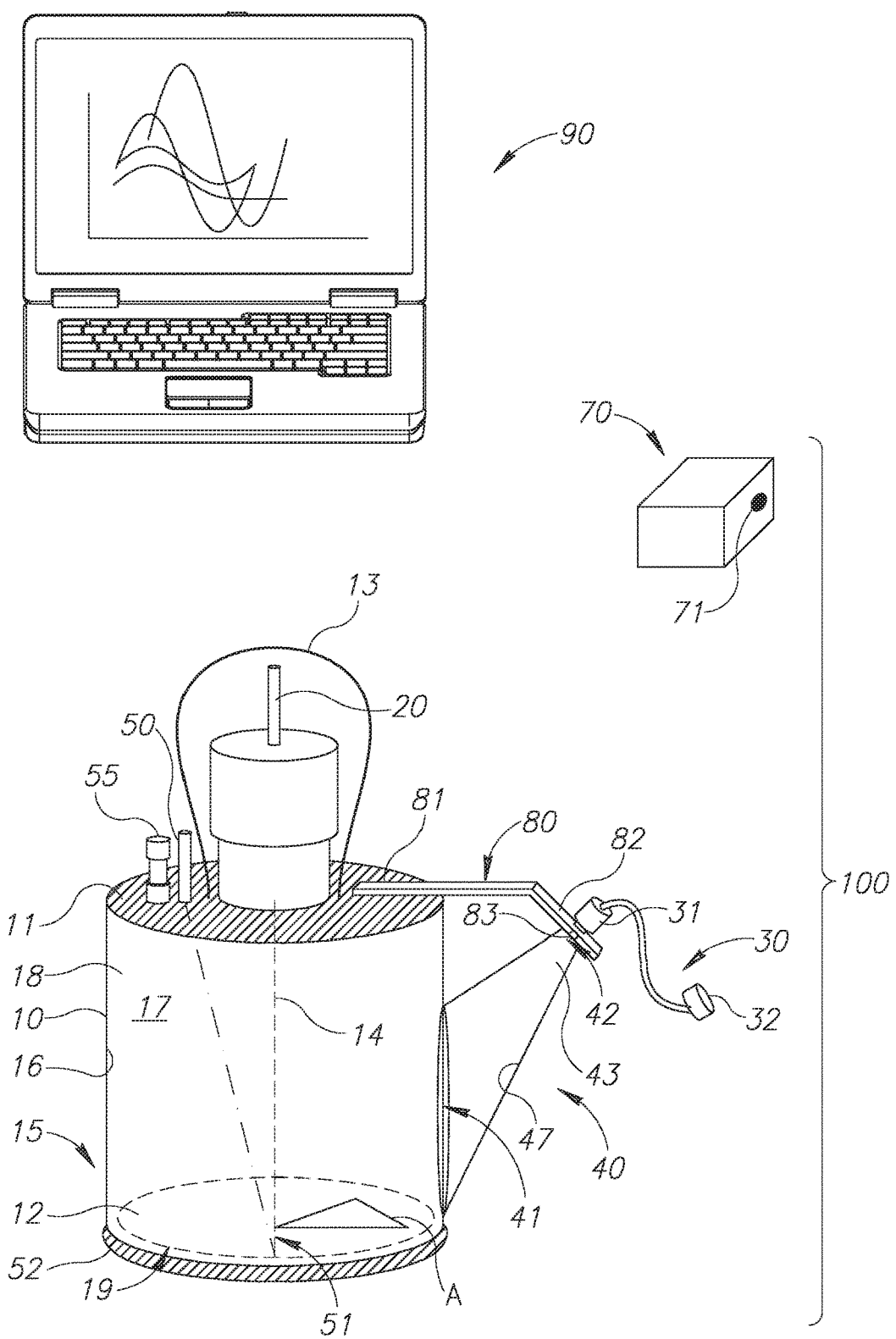
FIG. 1A schematically shows a perspective view of a SoilPro apparatus, in accordance with an embodiment of the disclosure.
Figure 1B:
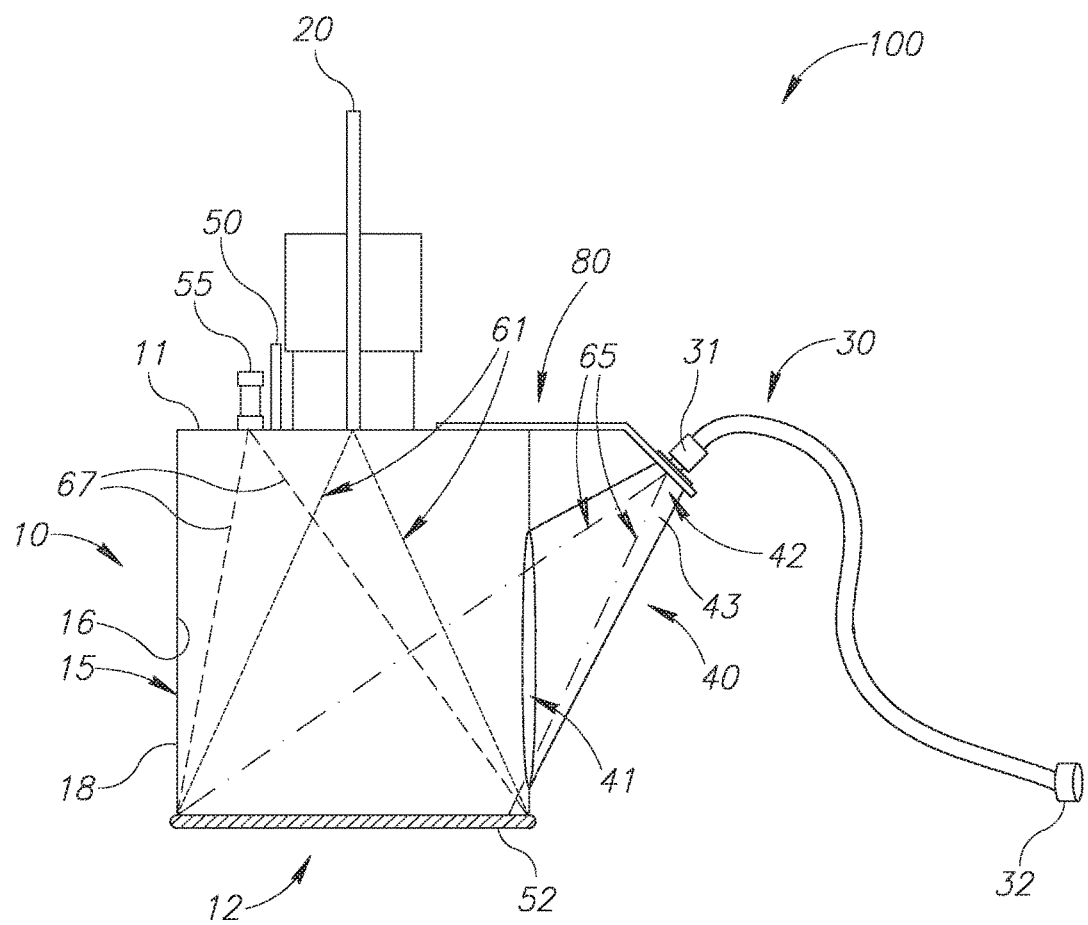
FIG. 1B schematically shows a cross section view of the SoilPro shown in FIG. 1A, in accordance with an embodiment of the disclosure.
Figure 2A:
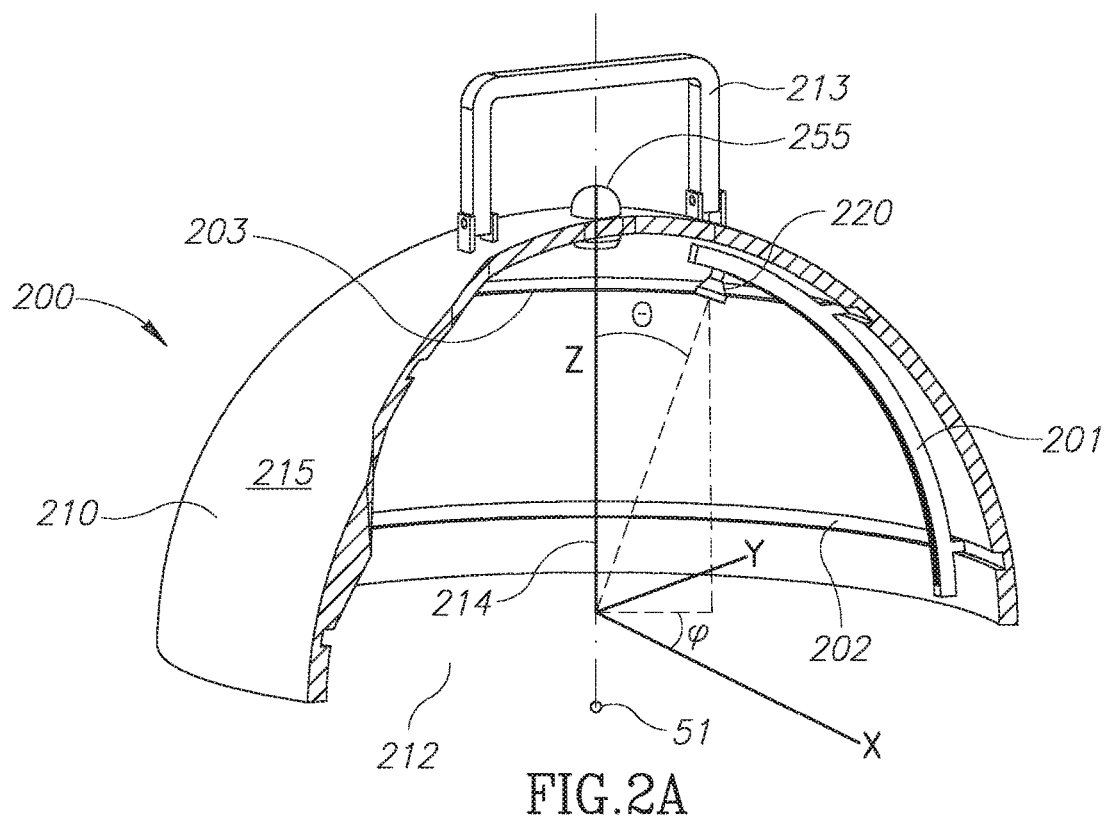
FIGS. 2A-2B schematically show a cutaway view of another embodiment of SoilPro having a hemispherical chamber, in accordance with an embodiment of the disclosure.
Figure 2B:
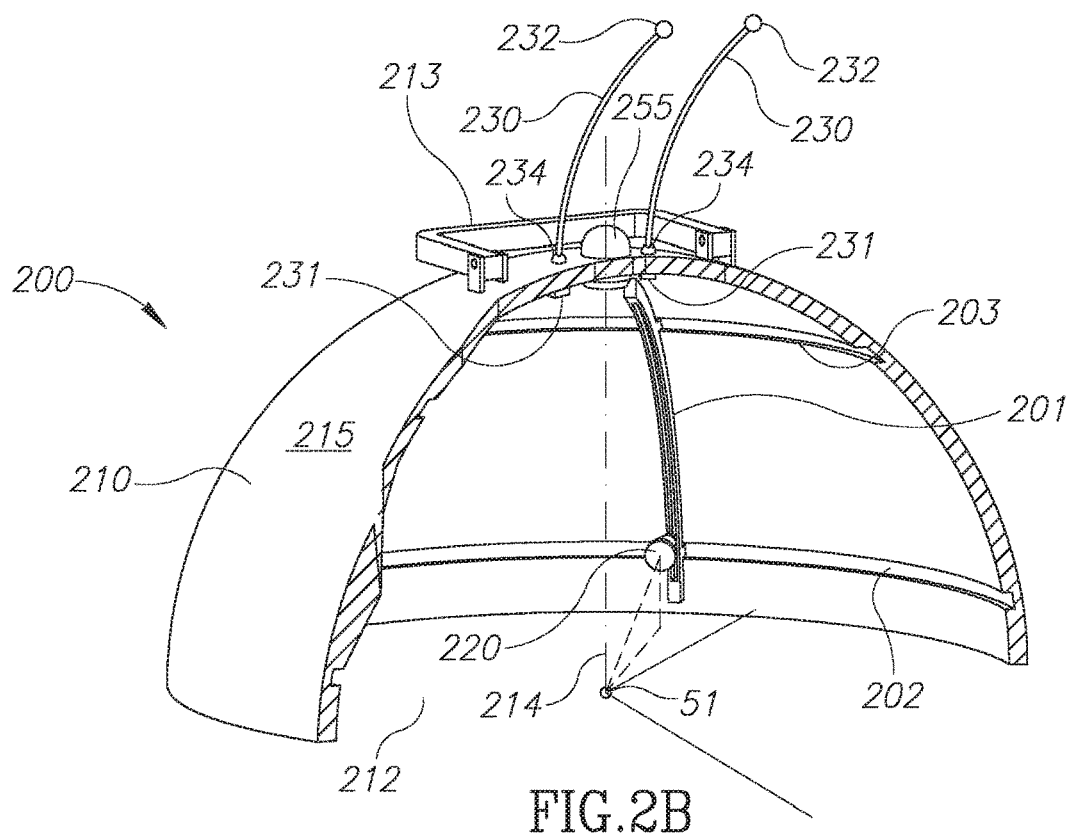

FIGS. 1A and 1B schematically show perspective and cross section views respectively of a SoilPro 100, in accordance with an embodiment of the disclosure. FIG. 2A-2B schematically show an embodiment of a SoilPro, having a hemispherical chamber and comprising a light source movable to different poses inside the housing, in accordance with an embodiment of the disclosure.

In the discussion, unless otherwise stated, adjectives such as "substantially" and "about" modifying a condition or relationship characteristic of a feature or features of an embodiment of the disclosure, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins SoilPro 100 comprises an optionally circularly cylindrical, "barrel shaped", housing, or chamber 10, having a top panel 11, and an open end 12, referred to as aperture 12, configured to be placed over a land sample. SoilPro 100 comprises a light source 20 optionally mounted to panel 11 of the chamber and configured to illuminate a land sample located in aperture 12. An optical fiber 30 is mounted to chamber 10, optionally by a support arm 80 and collimator 40. Collimator 40 opens into an internal volume 17 of SoilPro 100 so that an end 31 of the optical fiber collects light from light source 20 reflected by a land sample located at aperture 12. Optionally, a camera 55 is mounted to panel 11 to provide images of a land sample in aperture 12 that is illuminated by light from light source 20. A laser pointer 50 may be mounted to panel 11 to illuminate the land sample with a beam of light to generate a spot of light 51, which may be referred to as an optical fiducial, on the land sample, optionally substantially located at a center of aperture 12.

Chamber 10 may have an axis of rotation indicated by a dashed line 14 and comprises an optionally circularly cylindrical wall 15. Aperture 12 is optionally bounded by a planar circular boundary 19 indicated by a dashed circle, that lies in a plane of the aperture schematically indicated by a triangle icon "A", perpendicular to axis of rotation 14. When placed over a region of land, chamber 10 substantially prevents light from outside the chamber, such as solar light, from penetrating the chamber and light collected by optical fiber 30 is substantially limited to light from light source 20 that is reflected from the land sample. Optionally a cushion 52 as schematically shown in FIGS. 1A-1B, or a skirt, made of a flexible material, is attached to the chamber or the aperture boundary to aid in preventing outside light from penetrating through a space that may be formed between the chamber and a land sample when placed over the land sample. A handle 13 may be connected to panel 11 of the chamber, so that SoilPro 100 may relatively easily be carried from one location to another to acquire reflectance spectra for different land samples.

In an embodiment of the disclosure, light source 20 produces a light beam that is adjustable to intersect plane A at illumination intersections of different sizes that lie within aperture boundary 19 of aperture 12. The illumination intersection may substantially be congruent with aperture 12. A central axis of the beam of light, hereinafter, "beam axis", may coincide with axis of rotation 14 of the chamber and be referenced by numeral 14 which references the axis of rotation. In the cross section view schematically shown in FIG. 1B, dashed lines 61 indicate boundaries of a beam of light provided by light source 20. Boundaries 61 bound a field of illumination (FOI) of light source 20 in the cross section.

In an embodiment of the disclosure, light source 20 is configured to illuminate the land sample located within the illumination intersection, substantially uniformly with a relatively homogenous intensity. SoilPro 100 may comprise any of various mechanical and/or optical elements, such as a light reflector (not shown) and/or lens system for directing light from light source 20 towards the land sample, so that light from light source 20 may be focused to illuminate the land sample located at the aperture and substantially reduce illumination of internal surfaces of and/or features other than the land sample, within chamber 10.

It is noted that whereas light source 20 is described above and illustrated in the figures to have an illumination intersection within boundaries 19 at aperture 12 which illuminates substantially the entire land sample at the aperture, light source 20 may be focused to illuminate a portion of a land sample at aperture 12, or may be focused to illuminate a particular object or substance placed within aperture 12.

In an embodiment of the disclosure, internal surfaces 16 of chamber 10, and internal surface 47 of collimator 40, are colored black so that light from light source 20 and/or light reflected from a land sample located within aperture 12, which may interact with the internal surfaces, are likely to be absorbed. Light collected by optical fiber 30 is therefore substantially limited to light from light source 20 that is reflected by the land sample directly to optical end 31 of optical fiber 30. An amount of light reflected by internal surfaces of SoilPro 100 that reaches collecting end 31 may be comparatively negligible relative to the light reflected by the land sample directly to the collecting end.

Light source 20 may be any light source suitable for illuminating a land sample located in aperture 12 to acquire a reflectance spectrum for the land sample. Optionally, light source 20 emits light characterized by a spectrum similar to that of radiation emitted by of the sun and/or a spectrum matched to spectral sensitivity of a detector, such as that of a spectrometer used with SoilPro. In an embodiment, SoilPro 100 is constructed so that light source 20 may readily be replaced by another light source, for example by screwing or clipping a light source into a suitable socket comprised in SoilPro 100, having a different illumination spectral bandwidth without having to move SoilPro 100 or disturb components of SoilPro other than the light source. SoilPro 100 may therefore be operated to acquire a sequence of reflectance spectrum measurements in a relatively short period of time and under substantially same ambient conditions of, for example temperature and humidity, at different bandwidths of electromagnetic radiation, using different light sources.

Optionally a filtering wheel selector or other filtering device, is used to selectively transmit or reject a desired wavelength band of light from light source 20, such as a band of visible light, infrared (IR), near infrared (NIR), ultraviolet (UV), to determine a desired reflectance spectrum for a land sample responsive to light from the light source that illuminates the land sample.

In an embodiment of the disclosure, collimator 40, optionally has a funnel shape, and is connected to an outer surface 18 of cylindrical wall 15 of chamber 10. Collimator 40 is configured having an aperture 41 that opens into volume 17 of the chamber, and an aperture 42 at an end 43 of the collimator, which is distal to the chamber. Optical fiber 30 is mounted optionally to the distal end and gathers light reflected from the land sample that passes through apertures 41 and 42. In an embodiment of the disclosure, collimator 40 is configured to maintain and secure the optical fiber at a desired "collection" angle relative to light beam axis 14. Optionally the collection angle ranges between 30° to 60° so that optical fiber 30 collects light having a substantially Lambertian nature, characterized by an advantageous ratio of light from light source 20 that is reflected diffusely to collecting end 31 of the optical fiber 30 to light from the light source that is specularly reflected to collecting end 31. Optionally, collimator 40 and support arm 80 may be configured so that the collection angle is equal to about 45°.

In the cross section view schematically shown in FIG. 1B dashed lines 65 indicate boundaries of an instantaneous field of view (IFOV) of optical fiber 30 that define a cone of acceptance of the optical fiber for collecting light. Boundaries 65 of the IFOV, which may be referred to as IFOV 65, and an acceptance angle of the IFOV are determined by a NA of fiber 30. Optionally the acceptance angle has a range between 15°-45°, and preferably has an angle equal to about 25°. By changing the IFOV of fiber 30, optically coupling collecting end 31 of optical fiber 30 to an optical system, and/or adjusting a distance of fiber collecting end 31 from aperture 12, an intersection of IFOV 65 with plane A can be relatively easily adjusted so that an imaging intersection of the optical fiber is smaller than, congruent with, or larger than the illumination intersection of light source 20 with plane A. Collimator 40 through which light is gathered to enter collecting end 31 may have a size which is larger than boundaries 65 so that the collimator does not interfere with the IFOV of the optical fiber.

In an embodiment of the disclosure, and as schematically shown in FIG. 1A, and noted above, the configuration of optical fiber 30 at aperture 42 is maintained and secured by, optionally, a support arm 80. Support arm 80 comprises an end 81 assembled to surface 11 of chamber 10, and an end 82 assembled to end 43 of collimator 40. End 82 of support arm 80 may be configured having a through hole (not shown) through which collecting end 31 is able to collect light from the illumination intersection of light source 20 and plane A. Support arm 80 is assembled to the chamber and collimator optionally by, screws and bolts (not shown). Optionally, the support rod is welded to the chamber or assembled by any other connecting element used in the art.

Light collected by optical fiber 30 propagates along the optical fiber to reach output end 32 of the fiber. In an embodiment of the disclosure, a spectrometer 70 for detecting and measuring a reflectance spectrum of light reflected from the land sample, may be connected to the optical fiber by plugging output end 32 of the optical fiber into a matching socket 71 comprised in the spectrometer. In an embodiment of the disclosure, spectrometer 70, may be any spectrometer known in the art, such as an array spectrometer, scanning spectrometer, or hyperspectral imager. Measurements provided by the spectrometer provide a spectral fingerprint of the land sample located at the aperture.

The spectral fingerprint may be processed and analyzed by a controller 90, in communication with and optionally comprised in SoilPro 100. In an embodiment of the disclosure, controller 90 may be configured with suitable programs and databases so that the controller may receive a spectral fingerprint of the land sample and process the spectral fingerprint to provide additional information related to optionally chemical and/or physical makeup of soil in the land sample. By way of example, controller 90 may compare the reflectance spectrum data of a spectral fingerprint to reflectance spectrum data relating to chemical and/or physical materials and/or bacteria, stored in related databases comprised in or to which controller 90 has access. In an embodiment the related databases are cloud based. SoilPro 100 may therefore be operated to provide information relating to a presence or absence of a particular material or a group of materials in a land sample. In and embodiment of the disclosure, controller 90 may control SoilPro 100 and/or receive data from SoilPro over a wire or wireless communication interface comprised in SoilPro 100, such as mobile phone interfaces, Bluetooth and/or WiFi.

Controller 90 may comprise any electronic and/or optical processing and/or control circuitry, to provide and enable functionalities that SoilPro 100 may require to support acquiring and/or processing reflectance spectral measurements, in accordance with an embodiment of the disclosure. By way of example, controller 90 may comprise any one, or any combination of more than one of, a microprocessor, an application specific circuit (ASIC), field programmable array (FPGA) and/or system on a chip (SOC). The controller may comprise a non-volatile memory having any electronic and/or optical circuitry suitable for storing data and/or computer executable instructions and may, by way of example, comprise any one or any combination of more than one of a flash memory, random access memory (RAM), read only memory (ROM), and/or erasable programmable read-only memory (EPROM). Optionally, controller 90 is comprised in a smartphone, may be supported by processor and memory circuitry comprised in the smartphone that support smartphone functionalities.

Camera 55 referred to above may be operated to acquire images of the land sample at aperture 12 through, optionally, an aperture or port (not shown) in panel 11. The images may be processed to provide additional information of the land sample prior to, during, or after acquiring reflectance spectral measurements. The camera lens (not shown) may be adjusted so that a FOV of camera 55 intersects plane A at different size areas, "camera intersections" which lie within aperture boundary 19. Boundaries 67 indicate the camera's FOV, in the cross section view schematically shown in FIG. 1B. A camera intersection may be larger or smaller than the imaging intersection of the optical fiber and/or the illumination intersection of the light source within aperture 12. Optionally, the camera intersection is congruent with the imaging and/or illumination intersections.

In an embodiment of the disclosure, optical fiducial 51 (FIG. 1A) generated by laser pointer 50 referred to above may be used for validating proper alignment of components of SoilPro 100. By way of example, laser pointer 50 may direct a beam of light to a center of aperture 12 so that optical fiducial 51 on a land sample located in aperture 12 may substantially coincide with an intersection of axis of rotation 14 and the land sample. Controller 90 may control light source 20 to emit a constant and stable beam of light to illuminate a land sample in aperture 12 and/or to control camera 55 to acquire an image, a "reference image", of the land sample responsive to light from the light source that the land sample reflects. A reference image may be used to determine if light source 20 is relatively properly configured to illuminate the entire land sample at aperture 12 and/or if optical fiducial 51 is located at a desired location in the land sample. Additionally or alternatively, a reference image taken by camera 55 may be initiated by controller 90, to determine if FOV 65 of optical fiber 30 is advantageously configured to collect light reflected from the land sample, and optionally to determine an orientation of the imaging intersection with respect to the illumination intersection. Controller 90 may process the reference image from camera 55 to determine if components of SoilPro 100 are properly configured and/or aligned. If the reference image indicates that imaging intersection of optical fiber 30 is properly configured to include the illumination intersection or if it is congruent with the illumination intersection, the spectrometer may be indicated as advantageously receiving light reflected from the land sample via the optical fiber. Should the reference image indicate that imaging intersection is misaligned with aperture boundary 19, controller 90 may optionally be configured to provide a signal indicating that optical fiber 30 requires adjustment. In an embodiment of the disclosure, a measurement of light acquired by spectrometer 70 may be processed to determine whether optical fiducial 51 is located at the center of FOV 65 of optical fiber.

In an embodiment of the disclosure, chamber 10 has a diameter of about 24 centimeters (cm) and a height of about 25 cm, so that aperture 12 may confine a land sample having an area of about 400 cm$^2$. Walls of chamber 10 and collimator 40 are optionally 2 millimeter (mm) thick and made of aluminum, so that SoilPro 100 is configured to be relatively light weight and easily lifted to be moved to a location for acquiring a reflectance spectrum of a region of soil. Additionally, the aluminum walls provide relatively efficient heat conduction, and aid in moderating temperature changes inside SoilPro 100 during reflectance spectrum measurements, which can introduce errors into the measurements.

In an embodiment of the disclosure, controller 90 may be configured to operate SoilPro 100 by turning ON light source 20 for limited time intervals to moderate changes in ambient conditions inside the SoilPro that might be generated by heat from the light source. By way of example, an exposure time of the land sample to light from light source 20 is optionally determined by a temperature feedback loop mechanism controlled by controller 90 so that SoilPro 100 is operated at a time interval during which temperature of SoilPro 100 is within an advantageous, optionally predetermined range of temperatures. During operation of SoilPro 100, controller 90 may receive data acquired by a temperature sensor optionally comprised in SoilPro 100, provided to detect the internal temperature within chamber 10. In an embodiment of the disclosure, controller 90 is optionally preprogrammed to power OFF light source 20 when the temperature sensor provides a signal indicating that the temperature within the chamber has reached a value or range of values indicating overheating of SoilPro 100. Optionally, controller 90 may control operation of SoilPro 100 to operate at a preprogrammed time interval advantageous for collecting reflectance by the optical fiber. Controlling internal temperature within the SoilPro may control possible influences of dark noise on light reflected from the land sample, which may render measurement of spectral reflectance acquired by the spectrometer, inaccurate. In addition, a selected time interval for operation of SoilPro 100 may be determined to avoid changes in location of materials, such as liquids, in a land sample which may influence acquisition of a spectral fingerprint of the land sample during a series of measurements taken for a same land sample.

SoilPro 100 may comprise and/or be connectable to a suitable power source for powering its operation. The power source optionally comprises a portable battery. The power source optionally comprises a rechargeable battery. The rechargeable battery optionally comprises a charging socket for connecting the rechargeable battery to an electrical outlet and an indicator, such as a light indicator comprised in the power source to indicate whether the power source is charged. The power source may comprise a car charger. Optionally, the power source comprises a portable solar charger. Soil Pro 100 optionally comprises a power converter operable to provide light source 20 with a stabilized output voltage.

In an embodiment of the disclosure, a spectral fingerprint acquired for a land sample may be stored in a database comprised in a non-volatile memory (not shown), in controller 90, together with a geolocation of the land sample.

Whereas the description and figures above describe a SoilPro chamber having a cylindrical shape and particular dimensions, embodiments of the invention may have other configurations of chamber size and shape. Similarly, it is conceivable to have a collimator supporting the optical fiber having a shape different from the funnel shape described in the discussion above and in figures.

For example, FIGS. 2A and 2B, schematically shows a cutaway view of a SoilPro 200 comprising a hemispherical chamber 210 having an axis of rotation 214, and a light source 220 readily movable to illuminate a land sample at an aperture 212 of the chamber from various poses, that is various positions and illumination directions, from within chamber 210. A pose position of light source 220 may be defined by elevation and azimuth angles $\theta$ and $\varphi$ optionally measured from a z-axis and x-axis of a coordinate system for which the z-axis is coincident with axis of rotation 214. Poses of light source may be determined to correspond to locations and directions of illumination from which the sun may illuminate a land sample in aperture 212. Optionally, chamber 210 comprises a foldable carrying handle 213.

In an embodiment, light source 220 is mounted to and movable along an, optionally arcuate, guide rail 201 supported by upper and lower circular support guide rails 203 and 202, also referred to as support rails 203 and 202 respectively mounted to a wall 215 of chamber 210. Guide rail 201 is moveable along support guide rails 202 and 203 through an allowed range of azimuth angles, $\varphi$, about axis of rotation 214 optionally equal to about 360°. Optionally, at least one motor (not shown) couples guide rail to support rails 202 and 203 and is controllable by controller 90 to move the guide rail along the support rails about axis of rotation 214 to any desired azimuth angle $\varphi$ in the range of allowed azimuth angles. The at least one motor may comprise any suitable motor known in the art and may for example comprise a piezoelectric motor friction coupled to a support rail 202 or 203, or a stepper motor that couples guide rail 201 to a support rail via a gear arrangement. Light source 220 may similarly be coupled to arcuate guide rail 201 by at least one of any of various suitable motors, such as a stepper or piezoelectric motor, and a suitable gear or friction contact arrangement. The at least one motor may be controlled by controller 90 to move the light source along guide rail 201 to a desired elevation angle $\theta$. FIGS. 2A and 2B show light source 220 at different elevation $\theta$ and azimuth $\varphi$ pose angles. Optionally, the light source is mounted to a hinge or gimbal so that for a given elevation angle $\theta$ and azimuth angle $\varphi$, a direction along which the light source illuminates a land sample located within aperture 212 may be adjusted. Optionally, adjustment is controllable by controller 90. Power to power light source 220 and move it along guide and support rails 201, 202 and 203, and adjust direction of illumination for a given elevation and azimuth may be provided via sliding electrical contacts comprised in the guide and support rails.

A camera 255, which may be similar to camera 55 comprised in SoilPro 100 (FIG. 1A-1B), may be mounted to a top of hemispheric chamber 210 and is operable to acquire images of a land sample in aperture 212 of SoilPro 200. Optionally, camera 255 has an optical axis substantially coincident with axis of rotation 214 of the hemispheric chamber. SoilPro 200 may comprise an optical fiber 230 similar to optical fiber 30 of SoilPro 100, mountable in proximity to camera 255 by plugging it into a socket 234 in the wall 215 so that a collecting end 231 of the optical fiber protrudes inwardly into the chamber. As previously described with respect to SoilPro 100, an output end 232 of the optical fiber may be connected to a spectrometer to determine a spectrum of light from light source 220 that is reflected by the land sample and collected by the optical fiber. Optionally SoilPro 200 comprises more than one optical fiber, as schematically shown in FIG. 2B.

In an embodiment of the disclosure, control 90 may be programmed with a preprogrammed measuring program, having a defined pose, or series of poses from which light source 220, illuminates the land sample at aperture 212 and SoilPro 200 acquires various images and spectral reflection data. The program may further define an illumination period for each pose, an image scanning period and/or a number of images acquired during an illumination period.

Whereas light source 220 is describe to be controlled by a controller to be placed at various poses within the chamber, it is conceivable that light source 220 and guided rail 201 are manually operated to be moved to various poses. Further, whereas SoilPro 200 as schematically shown and described with reference to FIGS. 2A-2B comprises two support guide rails 202 and 203, in an embodiment SoilPro may have less than or more than two support guide rails for supporting guide rail 201 Optionally SoilPro 200 comprises a sensor (not shown) mounted on light source 220 which acquires coordinates of the light source and guide rail 201 to determine the light source position at any time during operation of the SoilPro and transmits the data to the controller for use in controlling the pose of light source 220.

It is noted that whereas in SoilPro 200 moveable light source 220 is mounted in a hemispherical chamber, a SoilPro having a moveable light source may have a chamber other than hemispherical. For example, a moveable light source may be mounted on guide and support rails mounted inside a circularly or elliptically cylindrical chamber.

Whereas the description above refers to an optical fiber mounted and fixed to the chamber, a SoilPro may comprise an optical fiber that is readily movable to different positions and different collection angles relative to light beam axis 14, in accordance with an embodiment of the disclosure.

It is noted that whereas a SoilPro in accordance with an embodiment of the disclosure is described in the text above and schematically illustrated in the figures, to illuminate a region of soil within an area of land and/or measure spectral reflectance from the region of soil, SoilPro 100 is not limited to acquiring measurements of a land sample. SoilPro 100 may be used to illuminate and measure a reflectance spectrum from substantially anything which can be placed within the aperture of the chamber such as an object, surface and/or a substance. SoilPro may for example acquire reflectance spectra for natural substances such as sand, rocks, bare soils, vegetation, artificial surfaces such as roadway asphalt, concrete, various floorings, and/or extraterrestrial surfaces. Furthermore, a surface within the aperture of SoilPro 100 is not limited to any particular geometry and/or environmental and/or climatic condition for operation of SoilPro 100. By way of example, SoilPro 100 may be used in a broad range of climatic conditions, weather, atmospheric, and/or sky conditions, since SoilPro may be operated to perform measurements in situ while substantially shielding the surface at the aperture from outside conditions, such as solar radiation, that may influence spectral measurements acquired by the SoilPro. SoilPro therefore enables acquiring during day or night relatively reproducible spectral measurements under various weather and/or various sky conditions, independent of whether it is hazy, cloudy, overcast, hot or cold, foggy, or dusty. SoilPro 100 obtains spectral measurements of a surface at the aperture while maintaining the surface's natural state at the time of the measurements. A SoilPro in accordance with an embodiment of the disclosure may therefore acquire repeated spectral measurements of the surface to obtain a spectral fingerprint of the surface at the aperture substantially independent of changes in ambient conditions of the external environment.

There is therefore provided in accordance with an embodiment of the disclosure, an apparatus for measuring spectral reflectance of a surface, the apparatus comprising: a chamber comprising a wall formed having an aperture defined by an aperture boundary; a light source mounted to the chamber and having a field of illumination (FOI) configured to intersect the aperture at an illumination intersection; and an optical fiber mounted to the chamber and having a field of view (FOV) configured to intersect the aperture at an imaging intersection; wherein the chamber is configured so that when the aperture is positioned on a surface the chamber substantially prevents light from entering a volume of the chamber. In an embodiment of the disclosure, the illumination intersection is controllable so that it overlaps only a portion of the aperture. In an embodiment of the disclosure, the illumination intersection is controllable so that it is substantially congruent with the aperture.

In an embodiment of the disclosure, the light source is controllable to illuminate the aperture from different poses, each pose defined by a position of the light source and an illumination direction along which the light source illuminates the aperture. Optionally, the light source is mounted to and movable along at least one guide rail to change a position that defines the pose. Optionally, the at least one guide rail comprises a plurality of guide rails. Optionally, motion of the light source along one of the plurality of guide rails changes an elevation angle of the light source inside the chamber. Optionally, motion of the light source along another of the plurality of guide rails changes an azimuth angle of the light source inside the chamber. Optionally, for a given position of the light source the light source is controllable to change the illumination direction that defines the pose. Optionally, the light source is mounted to a hinge and/or gimbal which is controllable to change the illumination direction of the pose.

In an embodiment, the apparatus may comprise a controller that controls pose of the light source. Optionally, the controller is programmable to automatically move the light source through a sequence of a plurality of different preset poses.

In an embodiment of the disclosure, the apparatus may comprise a collimator configured to collimate light that reaches the optical fiber.

In an embodiment of the disclosure, the imaging intersection is controllable to overlap only a portion of the aperture. In an embodiment of the disclosure, the imaging intersection is controllable so that it is substantially congruent with the aperture. In an embodiment of the disclosure, at least one of the illumination intersection and the imaging intersection is controllable so that the intersections are substantially congruent.

In an embodiment of the disclosure, the boundary of the aperture comprises a flexible material configured to operate as a light seal that prevents light from entering the volume of the chamber when the aperture is positioned on a surface.

In an embodiment of the disclosure, internal surfaces of the chamber are configured to absorb light provided by the light source.

In an embodiment of the disclosure, the apparatus may comprise a camera configured to image at least a portion of a surface located at the aperture. In an embodiment of the disclosure, the apparatus may comprise a spectrometer configured to receive light collected by the optical fiber from light reflected by a surface located in the FOV of the optical fiber.

It is further provided in accordance with an embodiment of the disclosure, a method for acquiring a reflectance spectrum of a surface, the method comprising: sealing the surface from ambient light; illuminating the surface with light in a desired spectral bandwidth; collecting light reflected by the surface from the illuminating light; and processing the collected light to provide the reflectance spectrum.

In an embodiment of the disclosure, illuminating comprises illuminating from a plurality of different light sources poses. In an embodiment of the disclosure, collecting comprises collecting light reflected from the surface at different collection angles. In accordance with an embodiment of the disclosure, the method may comprise imaging the surface with a camera.

In an embodiment of the disclosure, sealing comprises locating the surface in a chamber. In an embodiment, the method may comprise sealing light from entering the volume of the chamber with a flexible material.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. An apparatus for measuring spectral reflectance of a surface, the apparatus comprising:
   a chamber comprising a wall formed having an aperture defined by an aperture boundary;
   a light source mounted to the chamber and having a field of illumination (FOI) configured to intersect the aperture at an illumination intersection, and controllable to illuminate the aperture from different poses, each pose defined by a position of the light source and an illumination direction along which the light source illuminates the aperture; and
   an optical fiber mounted to the chamber and having a field of view (FOV) configured to intersect the aperture at an imaging intersection;
   wherein the chamber is configured so that when the aperture is positioned on a surface, the chamber substantially prevents light from outside the chamber from entering a volume of the chamber.

2. The apparatus according to claim 1, wherein the illumination intersection is controllable so that it is substantially congruent with the aperture.

3. The apparatus according to claim 1, wherein the light source is mounted to and movable along at least one guide rail to change a position that defines the pose.

4. The apparatus according to claim 3, wherein the at least one guide rail comprises a plurality of guide rails.

5. The apparatus according to claim 4, wherein motion of the light source along one of the plurality of guide rails changes an elevation angle of the light source inside the chamber.

6. The apparatus according to claim 5, wherein motion of the light source along another of the plurality of guide rails changes an azimuth angle of the light source inside the chamber.

7. The apparatus according to claim 1, wherein for a given position of the light source the light source is controllable to change the illumination direction that defines the pose.

8. The apparatus according to claim 7, wherein the light source is mounted to a hinge and/or gimbal which is controllable to change the illumination direction of the pose.

9. The apparatus according to claim 1, and comprising a controller that controls pose of the light source.

10. The apparatus according to claim 9, wherein the controller is programmable to automatically move the light source through a sequence of a plurality of different preset poses.

11. The apparatus according to claim 1, and comprising a collimator configured to collimate light that reaches the optical fiber.

12. The apparatus according to claim 1 wherein the imaging intersection is controllable to overlap only a portion of the aperture.

13. The apparatus according to claim 1 wherein the imaging intersection is controllable so that it is substantially congruent with the aperture.

14. The apparatus according to claim 1 wherein at least one of the illumination intersection and the imaging intersection is controllable so that the intersections are substantially congruent.

15. The apparatus according to claim 1 wherein the boundary of the aperture comprises a flexible material configured to operate as a light seal that prevents light from entering the volume of the chamber when the aperture is positioned on a surface.

16. The apparatus according to claim 1 wherein internal surfaces of the chamber are configured to absorb light provided by the light source.

17. The apparatus according to claim 1 and comprising a camera configured to image at least a portion of a surface located at the aperture.

18. The apparatus according to claim 1, and comprising a spectrometer configured to receive light collected by the optical fiber from light reflected by a surface located in the FOV of the optical fiber.

19. The apparatus according to claim 1, wherein the illumination intersection is controllable so that it overlaps only a portion of the aperture.

* * * * *